United States Patent [19]
Baraldi

[11] Patent Number: 5,939,432
[45] Date of Patent: Aug. 17, 1999

[54] THIOPHENES USEFUL FOR MODULATING THE ADENOSINE RECEPTOR

[75] Inventor: Pier Giovanni Baraldi, Ferrara, Italy

[73] Assignee: Medco Research, Inc., Research Triangle Park, N.C.

[21] Appl. No.: 08/959,758

[22] Filed: Oct. 29, 1997

[51] Int. Cl.[6] .......... A61K 31/505; A61K 31/44; C07D 495/02; C07D 495/12

[52] U.S. Cl. .......... 514/301; 514/258; 514/267; 514/291; 544/250; 544/278; 546/80; 546/114

[58] Field of Search .......... 514/258, 267, 514/291, 301; 544/250, 278; 546/80, 114

[56] References Cited

U.S. PATENT DOCUMENTS 5,585,385  12/1996  Natsugari et al. .......... 514/300

OTHER PUBLICATIONS

Amoah–Apraku, B. et al., "Selective Potentiation by an $A_1$ Adenosine Receptor Enhancer of the Negative Dromotropic Action of Adenosine in the Guinea Pig Heart," The Journal of Pharmacology and Experimental Therapeutics, vol. 266, No. 2, pp. 611–617 (1993).

Bhattacharya, Samita et al., "Effects of Long–Term Treatment with the Allosteric Enhancer, PD81,723, n Chinese Hamster Ovary Cells Expressing Recombinant Human $A_1$ Adenosine Receptors," Molecular Pharmacology, vol. 50, pp. 104–111 (1996).

Bhattacharya, Samita et al., "The Allosteric Enhancer, PD 81,723, Stabilizes Human $A_1$ Adenosine Receptor Coupling to G Proteins," Biochimica et Biophysica Acta, 1265: pp. 15–21, 1995.

Bruns, Robert et al., "Allosteric Enhancement of Adenosine $A_1$ Receptor Binding and Function by 2–Amino–3–benzoylthiophenes," Molecular Pharmacology, vol. 38, No. 6, pp. 939–949 (1990).

Bruns, Robert et al., "Structure–Activity Relationships for Enhancement of Adenosine $A_1$Receptor Binding by 2–Amino–3benzoylthiophenes," Molecular Pharmacology, vol. 38, pp. 950–958 (1990).

Cao, X et al., "Adenosine $A_1$ Receptor Enhancer, PD 81,723, and Cerebral Ischemia/Refperfusion Injusry in the Gerbil," General Pharmacology, vol. 26, No. 7, pp. 1545–1548 (1995).

Corral, Carlos et al., "Reacciones de Bischler y de Friedlander con 2–amino–3–aroil–tiofenos", Afinidad, Mar.–Apr. (1978).

Dennis, Don M. et al., "Modulation of Atrioventricular Nodal Function by Metabolic and Allosteric Regulators Endogenous Adenosine in Guinea Pig Heart," Circulation, vol. 94, No. 10, pp. 2551–2559 (1996).

Fortea, Joan, "Thieno[2,3–d]pyrimidine 3–oxides. Synthesis and N–Oxide Reactions of 4–Phenyl–and 4–Aminothieno [2,3–d]pyrimidine 3–oxides," Journal Für praktische Chemie, Band 317, Heft 5, pp. 705–711(1975).

Hromatka, O. et al., "Über die Nitrierung von 7–Chlor–5–phenyl–1 H–thieno[2,3–e]1,4–diazepin–2(3H)–on, "Monatshefte für Chemie, vol. 104, pp. 709–714 (1973).

Janusz, Cynthia A. et al., "Functional activity of the adenosine binding enhancer, PD 81,723, in the in vitro hippocampal slice", Brain Research, vol. 567, pp. 181–187 (1991).

Kollias–Baker, C. et al., "Novel Approach for Enhancing Atrioventricular Nodal Conduction Delay Mediated by Endogenous Adenosine," Circulation Research, vol. 75, No. 6, pp. 972–980 (1994).

(List continued on next page.)

Primary Examiner—Mukund J. Shah
Assistant Examiner—Brenda Coleman
Attorney, Agent, or Firm—Burns, Doane, Swecker & Mathis, L.L.P.

[57] ABSTRACT

The present invention relates to compounds of formulas (IA), (IB), and (IC):

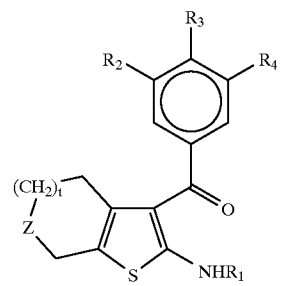

(IA)

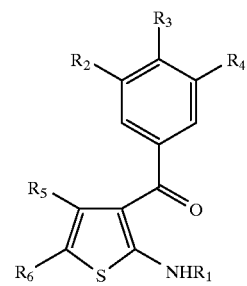

(IB)

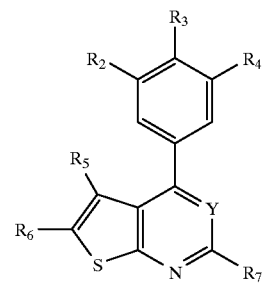

(IC)

the preparation thereof, pharmaceutical formulations thereof, and their use in medicine as allosteric adenosine receptor modulators for uses including protection against hypoxia and ischemia induced injury and treatment of adenosine-sensitive cardiac arrhythmias.

5 Claims, 4 Drawing Sheets

OTHER PUBLICATIONS

Kollias–Baker, C. et al., "Allosteric Enhancer PD 81,723 Acts by Novel Mechanism to Potentiate Cardiac Actions of Adenosine," Circulation Research, vol. 75, No. 6, 961–971 (1994).

Kollias–Baker, Cynthia, "The Allosteric Enhancer, PD 81,723, Potentiates the Cardiac Effects of Adenosine by Enhancing the Binding of Agonists to $A_1$ Adenosine Receptors," A Dissertation presented to the Graduate School of the University of Florida (1994).

Leung, E. et al., "Enhancement of Adenosine $A_1$ Receptor Functions by Benzoylthiophenes in Guinea Pig Tissues in Vitro," Archives of Pharmacology, vol. 352, No. 2, pp. 206–212, (1995).

Mizumura, Tsuneo et al., "PD 81,723, an Allosteric Enhancer of the $A_1$ Adenosine Receptor, Lowers the Threshold for Ischemic Preconditioning in Dogs," Circulation Research, vol. 79, No. 3, pp. 415–423 (Sep. 1996).

Mudumbi, Ramagopal V. et al., "Cardia Functional Responses to Adensoine by PD 81, 723, an Allosteric Enhancer of the Adenosine $A_1$ Receptor," American Journal of Physiology, vol. 264, pp. H1017–H1022, 1993.

Nakanishi, Michio et al., "Studies on Pcychotropic Drugs. 18.[1]Synthesis and Structure–Activity Relationships of 5–Phenyl–1,3–dihydro–2H–thieno[2,3–e][1,4] diazepin–2–ones," Journal of Medicinal Chemistry, vol. 16, No. 3, pp. 214–219 (1973).

Robba, Max et al, "No. 144—Thienopyrimidines. IX—Etude de la thieno[2,3–d] pyrimidines et de ses derives," Bulletin de la Societe Chimique de France, pp. 761–764 (1976).

Corral, Carlos et al., "Reacciones de Bischler y de Friedlander con 2–amino–3–aroil–tiofenos", Afinidad, Mar.–Apr. (1978).

CAS for Routh et al., Tachykinin Receptors In The Spinal Cord, Progress In Brain Research, vol. 104, pp. 93–108, 1995.

CAS for Chesselet et al., Ischemic Damage In The Striatum Of Adult Gerbils: Relative Sparing Of Somatostatinergic And Cholinergic Interneurons Contrasts With Loss Of Efferent Neurons, Experimental Neurology, vol. 110, No. 2, pp. 209–218, Nov. 1990.

CAS for Cragg et al., Tachykinin Antagonists In Carotid Body Responses To Hypoxia And Substance P In The Rat, Respiration Physiology, vol. 95, No. 3, pp. 295–310, Mar. 1994.

CAS for Benedek et al., Potentiation Of Thermoregulatory And Analgesic Effects Of Morphine By Calcium Antagonists, Pharmacological Research Communications, vol. 16, No. 10, pp. 1009–1018, Oct. 1984.

CAS for Ghio et al., Clinical Evaluation of Calcium–Antagonist Drugs, Journal Of Cardiovascular Pharmacology, vol. 20, pp. S71–S74, 1992.

CAS for Zhou et al., Effects Of Calcium Blockers On The Performance Of Left And Right Ventricles During Acute Hypoxia, Sheng Li Hseuh Pao, vol. 44, No. 3, pp. 237–243, Jun. 1992.

CAS for Ueno et al., Simultaneous Determination Of A New Dihydropyridine Calcium Blocker And Its Pyridine Metabolite In Dog Plasma By Column Switching High–Performance Liquid Chromatography With Electrochemical And Ultraviolet Detection, Analytical Scienc, 1991.

CHO-HuA1 Membranes

Comp. 20 concentration (log M)

CHO-HuA1 Membranes

CHO-HuA1 Membranes

THIOPHENES USEFUL FOR MODULATING THE ADENOSINE RECEPTOR

FIELD OF THE INVENTION

The present invention relates to certain thiophene derivatives and their use in the practice of medicine as allosteric modulators of adenosine receptors.

BACKGROUND OF THE INVENTION

Adenosine (Ado) is an autocoid (or local hormone) that modulates numerous functions in the cardiovascular and other organ systems. The actions of Ado are mediated by at least four subtypes of cell surface receptors called $A_1$, $A_{2a}$, $A_{2b}$, and $A_3$. Because the ubiquity of adenosine receptors (AdoRs) throughout the body of a human, their indiscriminate activation may cause undesirable side effects. Therefore, new drug design approaches to achieve organ selectivity are needed.

The overall function of Ado appears to be the regulation of the balance between oxygen (or energy) supply and consumption (or work). Ado increases oxygen supply by causing vasodilation and decreases oxygen consumption or work by inhibiting cellular functions, e.g., slowing of the heart rate. Consistent with this protective function, $A_1$AdoR agonists, Ado uptake blockers and Ado deaminase inhibitors have been shown to reduce cellular damage and dysfunction during hypoxia and ischemia. This protective role of Ado and $A_1$AdoR agonists has been shown in the heart, brain, liver, and intestines. This and other potentially beneficial actions of Ado have led to increased interest in the development of Ado-related drugs targeted to ameliorate conditions such as myocardial ischemia and stroke.

However, the widespread expression of Ado receptors and the lack of sufficiently selective adenosine agonists have been a major impediment to the successful development of direct-acting AdoR agonists to exploit the cytoprotective properties of Ado. Therefore, other pharmacological approaches such as allosteric modulators of Ado may prove to be a valuable alternative to direct-acting Ado agonists and nucleoside uptake blockers. Such agents should selectively modulate the response to Ado in only those organs or localized areas of a given organ in which production of Ado is increased. Thus, allosteric modulators of Ado function should provide a more selective therapeutic effect than direct-acting AdoR agonists. Their action will be limited to times and locations at which significant release of Ado occurs so that systemic side effects would largely be avoided.

Allosteric modulation of the actions of Ado on the $A_1$AdoR by several 2-amino-3-benzoylthiophenes on cultured cells, cardiac and brain preparations have been reported. The specificity of these compounds for $A_1$AdoRs have also been demonstrated.

A number of compounds known to modulate the action of neurotransmitters, hormones and peptides bind at sites distinct from, but functionally linked to, the primary recognition site of the respective receptors. This form of interaction between two different ligands at the same receptor protein, which may result in modulation in the form of enhancement or inhibition of each other's binding and function, is referred to as allosterism. Positive (enhancement) or negative (inhibition) allosterism are important mechanisms of action of drugs. For example, allosteric interactions between the GABA receptor and benzodiazepines, the atrial natriuretic factor (ANF) receptor and amiloride, the dextromethorphan binding site and ropizine, and the muscarinic receptor and gallamine have been described.

SUMMARY OF THE INVENTION

One aspect of the present invention is a compound selected from a group consisting of compounds of formulas IA, IB, and IC:

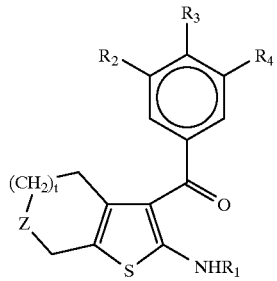

(IA)

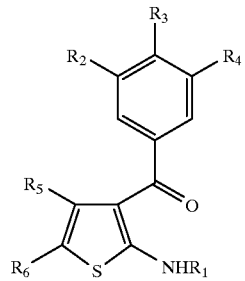

(IB)

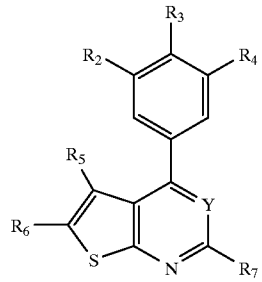

(IC)

wherein:
$R_1$ is hydrogen, lower alkyl, or haloacetyl;
$R_2$, $R_3$, and $R_4$ are independently hydrogen, halogen, lower alkyl, phenyl, lower alkenyl, lower alkanoyl, amino, trifluoromethyl, amino lower alkyl, nitro, or cyano;
t is 0, 1, 2, or 3;
Z is NH, N-$(Gr)_m(Am)_n(Alk)_p(Ph)_q$, or CH-$(Gr)_m(Am)_n(Alk)_p(Ph)_q$,
wherein
Gr is —SO$_2$—, —C(O)O—, or —C(O)—,
Am is —CH(NH$_2$)—, an amino acid residue, or an amino protected amino acid residue,
Alk is hydrogen, lower alkylene or lower alkenylene,
Ph is phenyl; phenyl substituted with one or more lower alkyl groups; or phenyl substituted with one or more nitro groups,
m is 0 or 1
n, p, and q are independently 0, 1, or 2, provided that at least one of m, n, p, and q is other than 0;
$R_5$ and $R_6$ are independently hydrogen, lower alkyl, or taken together form a lower alkenyl ring of 5 or 6 members, provided that if $R_2$, $R_3$, and $R_4$ are hydrogen, then, both $R_5$ and $R_6$ may be neither hydrogen nor methyl; further provided that if $R_2$ and $R_3$ are hydrogen while $R_4$ is trifluoromethyl or if $R_2$ and $R_4$ are hydrogen while $R_3$ is chloro, then both $R_5$ and $R_6$ may not be methyl;

$R_7$ is hydrogen or lower alkyl;

Y is Nitrogen, CH or $C(O)OR_8$; and

Wherein $R_8$ is hydrogen or lower alkyl.

A second aspect of the present invention is a method of allosterically modulating adenosine receptors in a mammal, including a human, comprising the administration to the mammal of an effective amount of a compound of formula IA, IB, or IC sufficient to moderate adenosine receptors.

A third aspect is a pharmaceutical formulation comprising a compound of formula IA, IB, or IC and one or more excipients. A fourth aspect are the novel chemical intermediates useful in the preparation of the compounds of formula IA, IB, or IC.

DETAILED DESCRIPTION OF THE INVENTION

Figure 1:
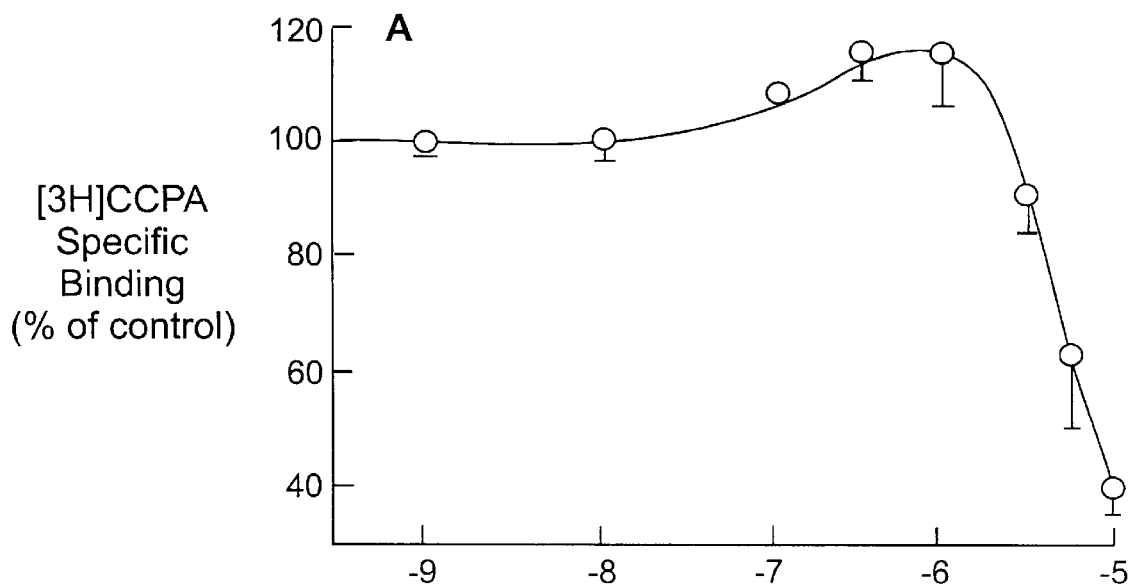
FIG. 1. Effect of the allosteric enhancer, 2-amino-3-benzoyl-6-(3-methylbut-2-en-lyl)-4,5,6,7-tetrahydrothieno[2,3-c]pyridine, Compound/Example number 20, on specific binding of the agonist [$^3$H]CCPA (FIG. 1A) and the antagonist [$^3$H]CPX (FIG. 1B) to membranes from Chinese hamster ovary (CHO) cells expressing recombinant $huA_1AdoR$.
Figure 1:
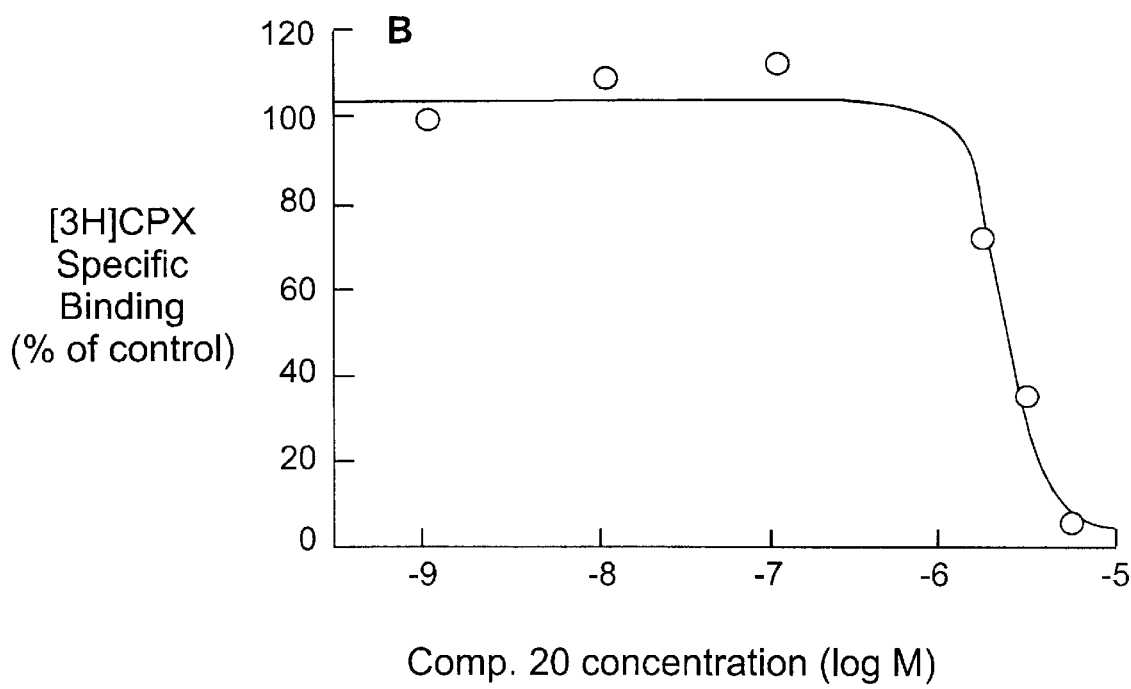

As used herein the term "lower alkyl" means a monovalent radical, straight or branched chain, derived from the corresponding alkane having one to ten carbon atoms, i.e., methyl, ethyl, propyl, Isopropyl, n-butyl, sec-butyl, t-butyl, pentyl (all isomers), etc. Likewise, "lower alkylene" means a divalent radical of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein the term "amino acid" means an alpha amino acid selected from those amino acids which naturally occur in proteins but without regard for specific stereochemical properties. The term "protected amino acid" means an amino acid of which the alpha amino group has been converted to a less reactive moiety, but a moiety which can be converted back to the amino group with relative ease. The terms "amino acid residue" and "amino acid moiety" are use synonymously herein.

Certain of the compounds of the present invention are sufficiently basic, (e.g., amino derivatives) or acidic (e.g., carboxylic acid derivatives) to form salts. Pharmaceutically acceptable salts of the compounds of formulas IA and IB are within the scope of the present invention. As will be understood by those skilled in the art, pharmaceutically acceptable salts include, but are not limited to, salts with inorganic acids such as hydrochloride, sulfate, phosphate, hydrobromide, and nitrate or salts with an organic acid such as malate, maleate, fumarate, tartrate, succinate, citrate, acetate, lactate, methanesulfonate, p-toluenesulfonate, palmoate, salicylate, and stearate. Other acids such as oxalic, while not in themselves pharmaceutically acceptable, may be useful as intermediates in obtaining the compounds of the invention and their pharmaceutical salts.

Particular compounds of the present invention include compounds of formulas IA, IB, and IC wherein $R_1$ is hydrogen, $R_2$, $R_3$, and $R_4$ are independently hydrogen, halogen, or trifluoromethyl, t is 0, 1, 2, or 3

Z is NH, N-$(CH_2)_{1-3}$ phenyl, N-(ethoxycarbonylmethyl), N-(2-t-butoxycarbonylamino-3-(4-hydroxyphenyl)-propion-1-yl), N-(3-methylbut-2-en-1-yl), N-(4-methylphenylsulphonyl), N-(4-nitro-(2-phenyleth-1-yl), or N-(benzyloxycarbonyl);

$R_5$ and $R_6$ are both hydrogen or both methyl, or $R_5$ and $R_6$ together form a cyclopentyl or cyclohexyl ring;

$R_7$ is hydrogen or methyl;

$R_8$ is ethyl.

Specific compounds of the present invention are:

| Compound/ Example Number | Compound Name |
| --- | --- |
| 2 | (2-amino-4,5-dimethyl-3-thienyl)-[(3,5-dichloro-4-amino)-phenyl)]methanone, |
| 5 | (2-amino-3-thienyl)-(4-chlorophenyl)methanone, |
| 7 | 2-amino-3-benzoyl-6-benzyloxycarbonyl-4,5,6,7-tetrahydrothieno[2,3-c]pyridine, |
| 8 | 2-amino-3-benzoyl-4,5,6,7-tetrahydrothieno[2,3-c]pyridine, |
| 9 | 2-amino-3-(4-chlorobenzoyl)-6-benzyloxycarbonyl-4,5,6,7-tetrahydrothieno[2,3-c]pyridine, |
| 10 | 2-amino-3-(4-chloro-benzoyl)-4,5,6,7-tetrahydrothieno[2,3-c]pyridine, |
| 11 | 2-amino-3-[3-(trifluoromethyl)-benzoyl]-6-(3-phenylprop-1-yl)-4,5,6,7-tetrahydrothieno[2,3-c]pyridine, |
| 13 | 2-amino-3-[3-(fluoromethyl)-benzoyl]-6-(phenylmethyl)-4,5,6,7,-tetrahydrothieno[2,3-c]pyridine, |
| 14 | 2-amino-3-(4-chloro-benzoyl)-6-(2-phenyleth-1-yl)-4,5,6,7-tetrahydrothieno[2,3-c]pyridine, |
| 15 | 2-amino-3-[3-(fluoromethyl)-benzoyl]-6-(2-phenyleth-1-yl)-4,5,6,7-tetrahydrothieno[2,3-c]pyridine, |
| 16 | 2-amino-3-(4-chloro-benzoyl)-6-(3-phenylprop-1-yl)-4,5,6,7-tetrahydrothieno[2,3-c]pyridine, |
| 18 | 2-amino-3-(4-chloro-benzoyl)-6-(ethoxycarbonylmethyl)-4,5,6,7-tetrahydrothieno[2,3-c]pyridine, |
| 20 | 2-amino-3-benzoyl-6-(3-methylbut-2-en-lyl)-4,5,6,7-tetrahydrothieno[2,3-c]pyridine, |
| 21 | 2-amino-3-(4-chloro-benzoyl)-6-[4-nitro-(2-phenyleth-1-yl)]-4,5,6,7-tetrahydrothieno[2,3-c]pyridine, |
| 22 | 2-amino-3-benzoyl-6-[4-nitro-(2-phenyleth-1-yl)]-4,5,6,7-tetrahydrothieno[2,3-c]pyridine, |
| 23 | 2-amino-3-benzoyl-6-[2-t-butoxycarbonylamino-3-(4-hydroxyphenyl)-propion-1-yl]4,5,6,7-tetrahydrothieno[2,3-c]pyridine, |
| 24 | 2-amino-3-benzoyl-4,5,6,7-tetrahydrobenzo[b]thiophene, |
| 25 | 4-phenyl-5,6,7,8-tetrahydro[1]benzothieno[2,3-d]pyrimidine |
| 26 | 2-methyl,3-ethoxycarbonyl-4-phenyl-5,6,7,8-tetrahydro[1]benzothieno[2,3-b]pyridine |
| 27 | 2-Amino-3-(4-bromobenzoyl)-cyclopenta[b]thiophene, and |
| 28 | 2-amino-3-benzoyl-6-(4-methylphenylsulphonyl)-4,5,6,7-tetrahydrothieno[2,3-c]pyridine. |

Those skilled in the art of organic chemistry will appreciate that reactive and fragile functional groups often must be protected prior to a particular reaction, or sequence of reactions, and then restored to their original forms after the last reaction is completed. Usually groups are protected by converting them to a relatively stable derivative. For example, a hydroxyl group may be converted to an ether group and an amino converted to an amide or carbamate. Methods of protecting and de-protecting, also known as "blocking" and "de-blocking," are well know and widely practiced in the art, e.g., see T. Green, *Protective Groups in Organic Synthesis,* John Wiley, New York (1981) or *Protective Groups in Organic Chemistry,* Ed. J. F. W. McOmie, Plenum Press, London (1973).

Synthesis of Compounds

Compounds of formula IB may be conveniently prepared according to Scheme 1.

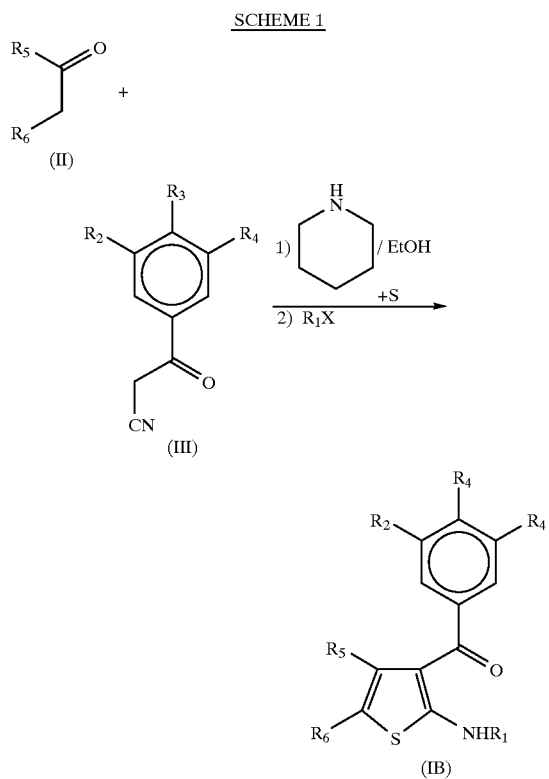

formula (III), benzophenone derivatives, may be prepared by methods of the art or conveniently according to Scheme 2.

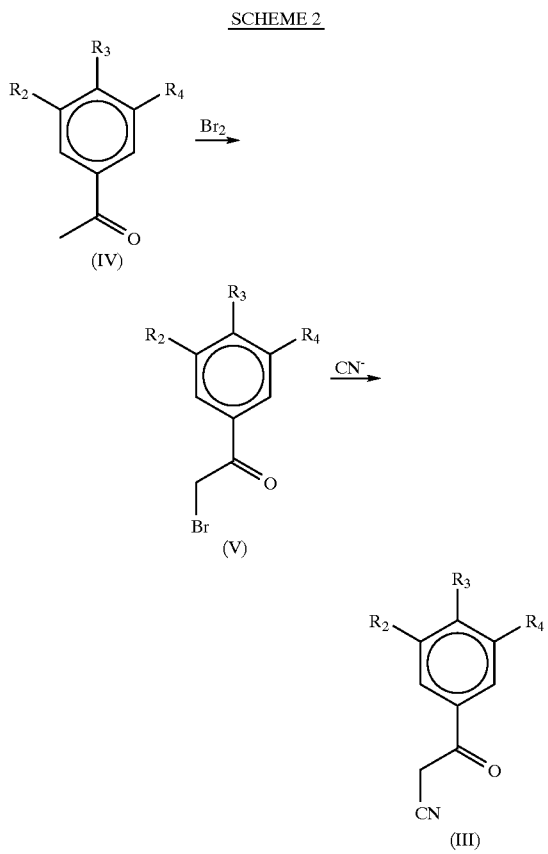

In Scheme 2 a compound of formula (IV), a substituted acetophenone, is alpha brominated with molecular bromine in a protic, polar solvent, such as acetic acid to yield the corresponding alpha bromo compound of formula (V). The compound of formula (III) is produced by reacting the compound of formula (V) with a source of cyanide ions, such as sodium or potassium cyanide, in a polar solvent, such as water, ethanol, or a mixture thereof.

In Step 1 a compound of formula (II) is reacted with a compound of formula (III) in the present of morpholine and molecular sulfur in a protic solvent, such as ethanol, at about 50° to about 65° C. for about an hour to yield a compound of formula IA wherein R1 is hydrogen.

Compounds of formula (IA) wherein $R_1$ is other than hydrogen may be prepared according to Step 2 by reacting a compound of formula (IB) from Step 1, wherein $R_1$ is hydrogen, with $R_1X$ (wherein $R_1$ is other than hydrogen, and X is a leaving group). For a discussion of nucleophilic displacement reactions and leaving groups see standard organic chemistry texts such as J. March, *Advanced Organic Chemistry,* chap. 10, John Wiley & Sons, New York (1985). Compounds of formula (II) are commercially available or may be prepared by methods of the art. Compound of

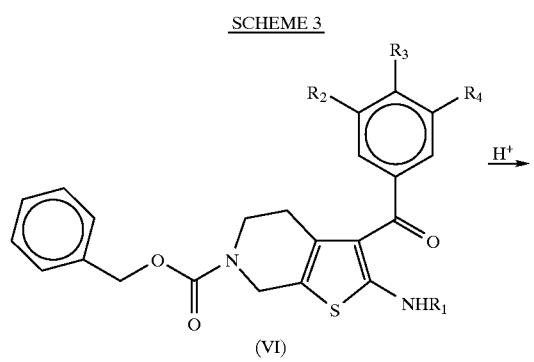

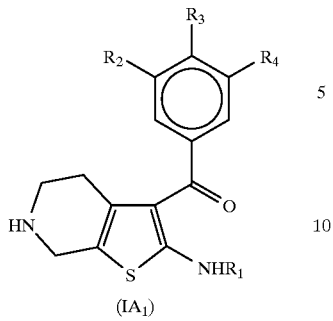

(IA$_1$)

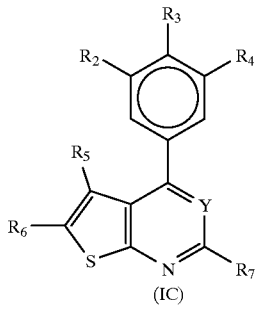

(IC)

As shown in Scheme 3, a compound of formula (IA$_1$) wherein Z is NH may be prepared by hydrolyzing the CO-N urethane linkage of a compound of formula (VI) under acidic conditions, e.g., hydrogen bromide in acetic acid.

In turn, a compound of formula (VI) may be prepared in a similar manner as the reaction of Scheme 1 by substituting a compound of formula (II) with a corresponding amount of a compound of formula (VII). It may be necessary to

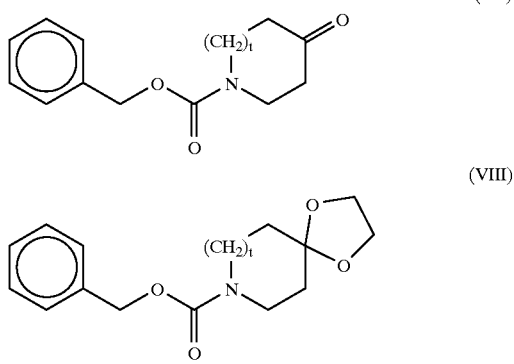

protect the carbonyl group of the piperidinone moiety during the synthesis of a precursor compound, e.g., by converting it to an ethylenedioxy derivative as seen in formula (VIII). The protecting or blocking group is removed after the synthesis of a compound of formula (VIII) to generate a compound of formula (VII).

Compounds of formula (IA) wherein Z is a substituted nitrogen, i.e., N-(Gr)$_m$(Am)$_n$(Alk)$_p$(Ph)$_q$, may be prepared by nucleophilic displacement by reacting a compound of the formula X-(Gr)$_m$(Am)$_n$(Alk)$_p$(Ph)$_q$, wherein X is a leaving group (see March, supra), in a polar solvent in the presence of a weak base such as sodium or potassium carbonate or a tertiary amine.

SCHEME 4

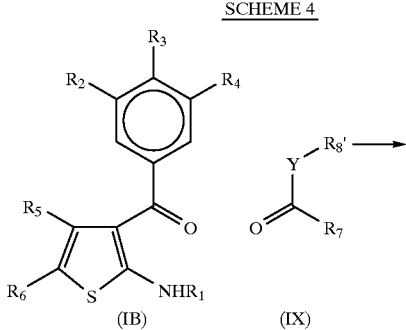

According to Scheme 4, a compounds of formula (IC), can be prepared from the corresponding compound of formula (IB), wherein R$_1$ is hydrogen, by reacting with a compound of formula (IX) in a protic, polar solvent, such as ethanol, in the presence of a strong base such as sodium ethylate to form the pyridine moiety. (If Y is nitrogen, then R$_8$' is H$_2$, and if Y is CH then R$_8$' is C(O)OR$_8$.) This reaction can conveniently be carried out by mixing the reactants, solvent and base at about 0° C. followed by heating at reflux for about 10 hours. A compound of formula (IC) wherein Y is nitrogen, i.e., R$_8$ is H$_2$, can be prepared from the corresponding compound of formula (IB) by reaction with a R$_7$—COONH$_2$, e.g., formamide, if R$_7$ is hydrogen, at about 180° C. for about 5 hours.

Compounds of formula (IA) wherein Z is N-(Gr)$_m$(Am)$_n$ (Alk)$_p$(Ph)$_q$, and Am is an amino acid or an amino acid with the amino group protected, and m, p, and q are 0, may be prepared by reacting the corresponding compound wherein Z is NH with a protected derivative of an amino acid. An example of a protected amino acid is BOC-tyrosine ("BOC-Tyr-OH") wherein "BOC" is —COOC(CH$_3$)$_3$. Preferably the reaction is run in a polar, aprotic solvent, such as dimethylformamide. Preparation of BOC derivative of amino acids are well known in the art of protein and peptide chemistry. If desired the BOC moiety may be removed by standard means of the art to restore the amino acid residue.

Utility

Compounds of this invention are useful for:

Protection against hypoxia and/or ischemia induced injuries (e.g., stroke, infarction);

Treatment of adenosine-sensitive cardiac arrhythmias;

antinociception (i.e., analgesics);

anticonvulsants; and

Other indications for which A$_1$AdoR agonists are used.

The amount of compound of the present invention required to be effective as an allosteric modulator of an adenosine receptor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 μg/kg to about 10 mg/kg body weight per day, preferably in the range of about 1 mg/kg to about 3 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 75 mg to about 220 mg per day, and a typical dose would be about 150 mg per day. If discrete multiple doses are indicated, treatment might typically be 50 mg of a compound of the present invention given 3 times per day.

Binding Assays

The prototypical allosteric enhancer PD 81,723, (prepared in Example 4; see Bruns, et al., *Mole. Pharm.*, 38:939 (1990), Cao et al., *Gen Pharmac.* 26:1545 (1995), and Amoah-Apraku et al., *J. Pharm. Exper. Ther.* 266(No.2):611 (1993)) has both enhancing and inhibitory activity at the $A_1$,AdoR. Therefore, the affect of a novel series of benzoylthiophene derivatives were determined on both the agonist [$^3$H]CCPA and the antagonist [$^3$H]CPX binding to membranes prepared from CHO cells stably expressing the human $A_1$ AdoR (CHO-hu$A_1$ AdoR). The enhancing activity was estimated by the magnitude of the increase in [$^3$H]CCPA binding whereas the inhibitory and (or antagonistic) activity was evaluated by the potency of the benzoylthiophene derivatives to compete for the specific binding of [$^3$H]CPX. The method used for the preparation of the membranes of CHO cells expressing hu$A_1$ AdoR, and the protocols for the radioligand binding assays are described by Kollias-Baker, et al., (*JPET*, 281, 761(1997) and *Circ. Res.*, 75, 961 (1994)).

Functional Assays

In previous studies (Amoah-Apraku, et al., *J. Pharmacol Exp. Ther.*, 266, 611 (1993) and Kollias-Baker, supra) the prototypical allosteric enhancer PD 81,723 was shown to selectively enhance $A_1$ AdoR-mediated prolongation of the stimulus to His (S-H) bundle interval (negative dromotropic effect) but did not increase the $A_{2a}$AdoR-mediated coronary vasodilation caused by Ado. Therefore, the effect of compound 20 on the negative dromotropic action of Ado in guinea pig isolated perfused hearts was determined. The guinea pig isolated perfused heart preparation and the methods for recording His bundle electrograms and measuring the S-H intervals have been previously reported.

Results

Radioligand Binding Assays

Figure 2:
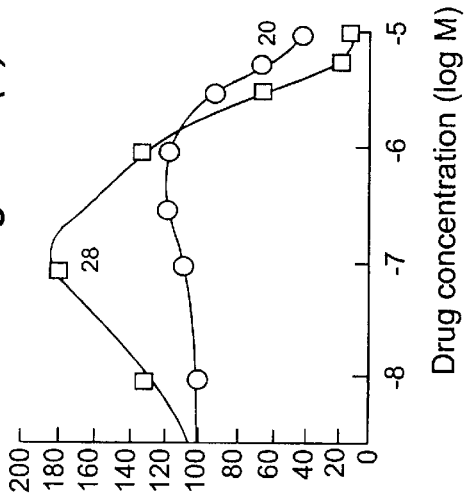
FIGS. 2 and 3 show the results of assays for specific binding of the agonist [$^3$H]CCPA.
Figure 2:
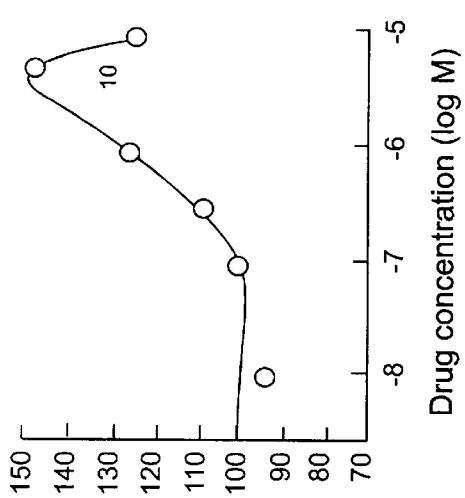
Figure 2:
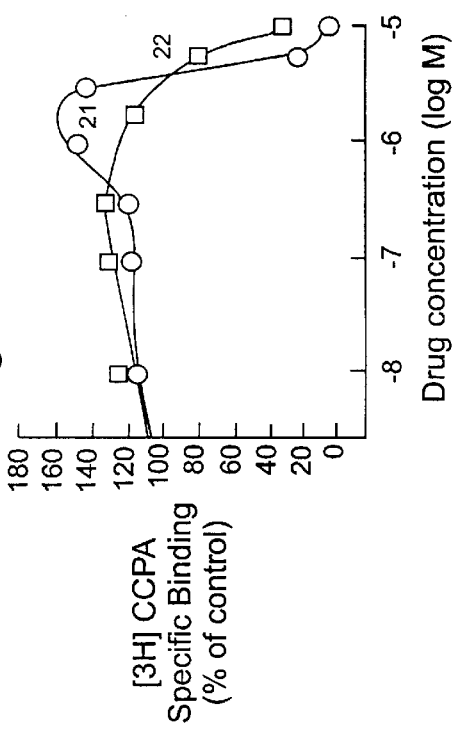
Figure 2:
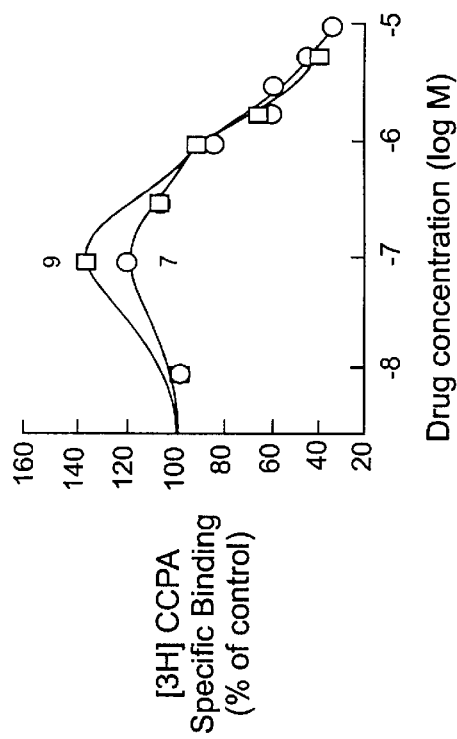
Figure 3:
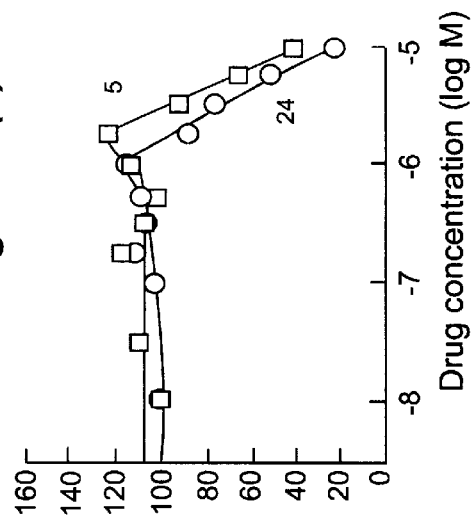
Figure 3:
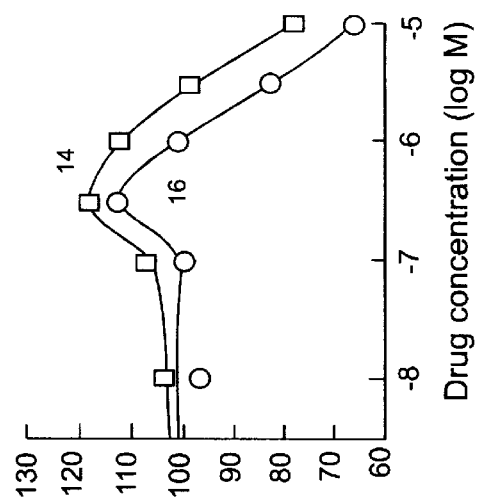
Figure 3:
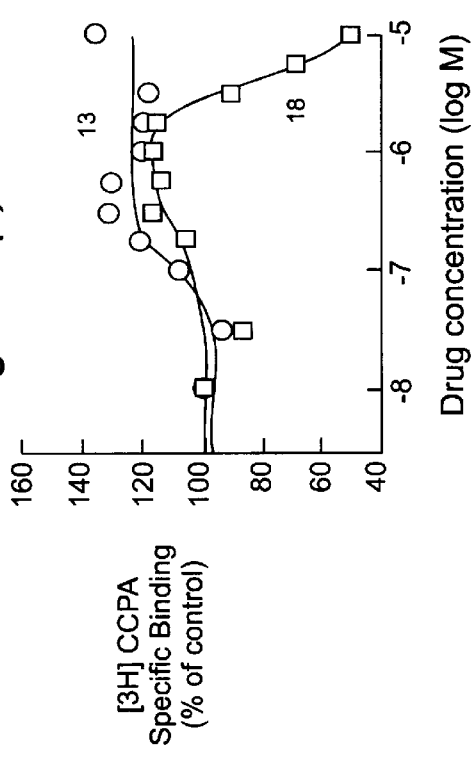
Figure 3:
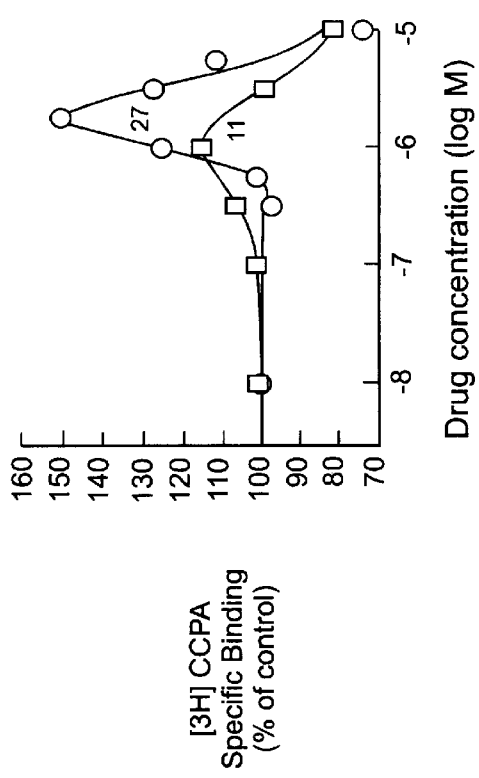

The effect of the benzoylthiophene derivative compound 20 on agonist and antagonist binding to CHO cells expressing the recombinant hu$A_1$AdoR was investigated. Specifically, the effects of compound 20 on the binding of the agonist radioligand [$^3$H]CCPA (2 nM) and the antagonist radioligand [$^3$H]CPX (1 nM) to recombinant CHO-hu$A_1$, AdoR were determined. As shown in FIG. 1A, the effect of compound 20 on the specific binding of [$^3$H]CCPA was biphasic, at concentrations up to 7 $\mu$M it increased but thereafter it decreased the specific binding of [$^3$H]CCPA. In contrast, compound 20 did not enhance the binding of the antagonist radioligand [$^3$H]CPX and at concentrations greater than 1 $\mu$M decreased the specific binding of [$^3$H] CPX, see FIG. 1B. The values are mean ±SEM of 4 hearts. Each data point represents mean ±SEM specific binding with determinations from 2–3 experiments. FIGS. 2 and 3 are similar to FIG. 1A but show the result of [$^3$H]CCPA studies on other compounds of the present invention.

Functional Studies

Figure 4:
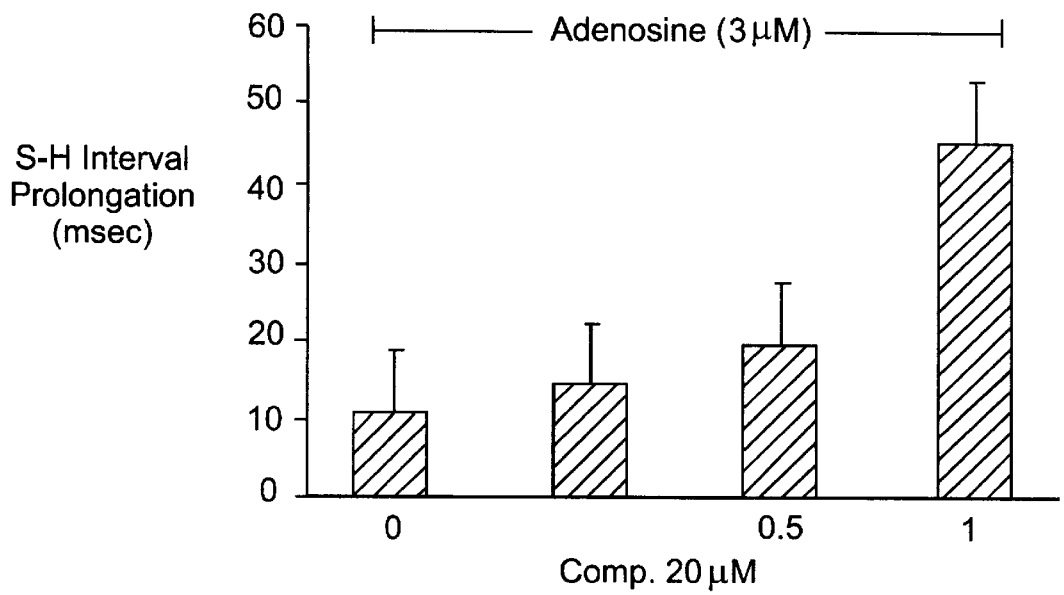
FIG. 4A. Concentration-dependent potentiation of the negative dromotropic effect (S-H interval prolongation) of adenosine by Compound 20 in guinea pig isolated hearts.
FIG. 4B. The effect of the $A_1AdoR$ antagonist CPX on the enhancement by Compounds 20 of the negative dromotropic action of adenosine.
Figure 4:
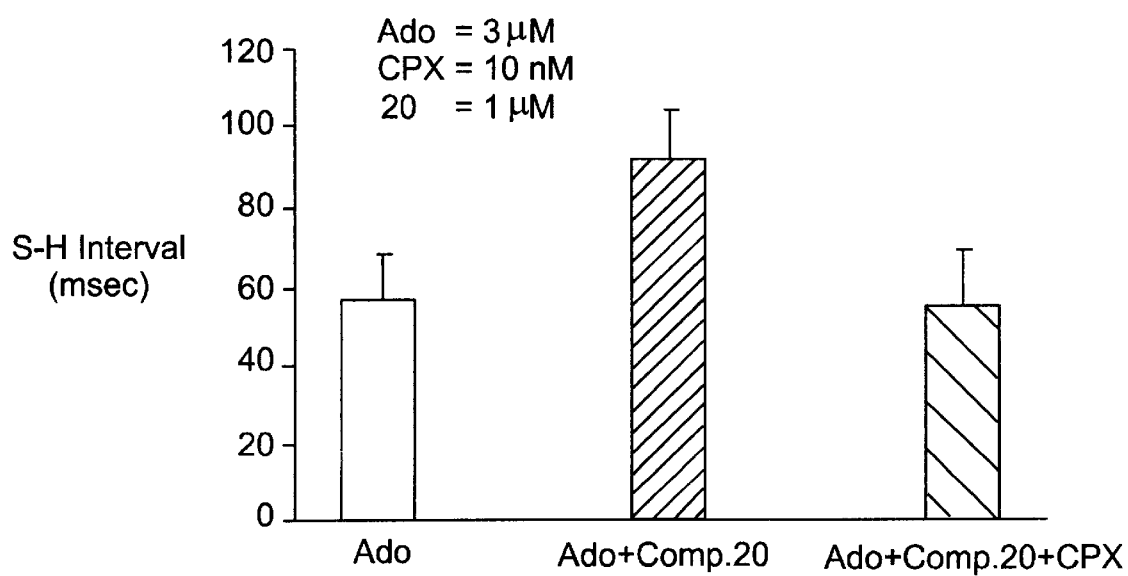

Consistent with the results of the radioligand binding assays, compound 20 enhanced the negative dromotropic effect (S-H interval prolongation) caused by Ado in a concentration-dependent manner (FIG. 4A). In pressure of 1 $\mu$M compound 20, 3 $\mu$M adenosine caused 2° A-V block in 2 of 4 hearts. The values are mean ±SEM of 4 guinea pigs. For instance, 0.1, 0.5 and 1.0 $\mu$M compound 20 enhanced the S-H prolongation induced by 3 $\mu$M Ado by 32%, 77%, and 311%, respectively. At 1.0 $\mu$M compound 20, the negative dromotropic effect of Ado was maximal, eliciting 2° A-V block in 2 of 4 hearts. In contrast, in the absence of compound 20, the same concentration of Ado (3 $\mu$M) prolonged the S-H interval by 11∓3 msec. To demonstrate that the enhancement of the dromotropic effect of Ado by compound 20 was mediated by activation of $A_1$AdoRs, prolongation of S-H interval caused by Ado in the presence of compound 20 was shown to be reversed by 10 $\mu$M of the $A_1$AdoR antagonist CPX (FIG. 4B). The reversal of the effects of compound 20 by CPX establishes that the enhancement was mediated through the $A_1$AdoR.

Formulations

Formulations of the present invention for medical use comprise an active compound, i.e., a compound of formula (IA), (IB) or (IC), together with a pharmaceutically acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (IA), (IB) or (IC) together with a pharmaceutically acceptable carrier thereof.

The formulations include, but are not limited to, those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise sterile aqueous preparation of the active compound which is preferably isotonic with the blood of the recipient. Thus, such formulations may conveniently contain distilled water, 5% dextrose in distilled water or saline. Useful formulations also comprise concentrated solutions or solids containing the compound of formula (I) which upon dilution with an appropriate solvent give a solution suitable for parental administration above.

Topical formulations include ointments, creams, gels and lotions which may be prepared by conventional methods known in the art of pharmacy. In addition to the ointment, cream gel, or lotion base and the active ingredient, such topical formulation may also contain preservatives, perfumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

EXAMPLES

The following examples illustrate aspects of this invention but should not be construed as limitations. The symbols and conventions used in these examples are intended to be consistent with those used in the contemporary, international, chemical literature, for example, the *Journal of the American Chemical Society and Tetrahedron.*

Example 1

(2-Amino-4,5-dimethyl-3-thienyl)-(phenyl) methanone

Compound 1

A. General Procedure for the Preparation of Phenacylbromides, the Compounds of Formula (V).

A solution of bromine (55 mmol) in acetic acid (50 mL) is added dropwise to an acetophenone (50 mmol), which is a compound of formula (IV), in glacial acetic (100 ml) in half an hour, with stirring. The resulting suspension is heated at 50° C. for an hour, and then poured into ice water (500 mL). The precipitated phenacyl bromide, a compound of fomula (V), is filtered and washed with cold water three times, and finally crystallized from ethanol. (See Rather and Reid, *J.Am.Chem.Soc.* 41, 77 (1919)).

B. General Procedure for the Preparation of Substituted Benzoyl Acetonitriles, the Compounds of Formula (III)

A phenacyl bromide as prepared in Step A, above, in ethanol is reacted with an aqueous solution of potassium cyanide dissolved in distilled water. The reaction is monitored by TLC control and during this time the solution changes color from yellow-orange to yellow-red. When the reaction is complete, crushed ice is added in a large amount and the solution is acidified with acetic acid. The precipitated corresponding benzoyl acetonitriles is filtered and washed with cold water then air dried.

C. (2-amino-4,5-dimethyl-3-thienyl)-(phenyl)methanone

A mixture of equimolar amounts of methylethyl ketone (0.01 mol), which is a compound of formula (II) wherein $R_5$ and $R_6$ are methyl, benzoyl acetonitrile (0.01 mol), which is a compound of formula (III) wherein $R_2$, $R_3$, and $R_4$ are hydrogen, sulfur (0.01 mol) and morpholine (0.01 mol) in ethanol (4 mL) was stirred and heated at 60° C. for an hour (TLC control). After this time, the suspension was left standing overnight, the mixture was poured into water and the precipitated solid was extracted with ethyl acetate (3×50 mL). The organic layers are dried on magnesium sulfate and evaporated under vacuum. The crude product was chromatographed on silica gel column using mixtures of ethyl acetate and petroleum ether.

(m.p. 140–141° C., 80% yield). 1H-NMR: (CDCl$_3$):1.53 (s, 3H), 2.13 (s, 3H); 6.44 (sb, 2H); 7.43–7.54 (m, 5H).

Examples 2–6

Compounds 2–6

The following compounds of formula (IB) are prepared by the procedure of Scheme 1 taught herein above, and in an analogous manner to Example 1 using appropriate precursor compounds of formula (II) and formula (III). If the desired compounds of formulas (II) and (III) are not commercially available, they may be prepared according to Example 1, sections A and B.

2: (2-amino-4,5-dimethyl-3-thienyl)-[(3,5-dichloro-4-amino)-phenyl)]methanone
(m.p. 155–157° C., 88% yield). 1H-NMR: (CDCl$_3$):1.71 (s, 3H), 2.16 (s, 3H); 4.79 (sb, 2H); 6.03 (sb, 2H); 7.48 (s,2H).

3: (2-amino-4,5-dimethyl-3-thienyl)-(4-chloro-phenyl) methanone
(m.p. 128–130° C., 89% yield). 1H NMR: (CDCl$_3$):1.54 (s, 3H), 2.13 (s, 3H); 6.47 (sb, 2H); 7.35–7.48 (m, 4H).

4: (2-amino-4,5-dimethyl-3-thienyl)-[3-(trifluoromethyl)-phenyl]methanone
(m.p. 103–105° C., 78% yield); 1H NMR: (CDCl$_3$):1.48 (s, 3H), 2.13 (s, 3H); 6.67 (sb, 2H); 7.54–7.75 (m, 4H).

5: (2-amino-3-thienyl)-(4-chlorophenyl)methanone
(m.p. 178–180° C., 81% yield). 1H NMR: (DMSO-d6) 6.27 (d, 1 H), 6.72 (d, 1 H); 7.52–7.63 (m, 4H); 8.39 (sb, 2H).

6: (2-amino-3-thienyl)-phenylmethanone
(m.p.150–152° C., 75% yield). 1H NMR: (CDCl$_3$): 6.11 (d, 1H), 6.87 (d,IH); 7.05 (sb, 2H); 7.3–7.7 (m, 5H).

Example 7

2-Amino-3-benzoyl-6-benzyloxycarbonyl-4,5,6,7-tetrahydrothieno[2,3-c]pyridine

Compound 7

A. Preparation of 8-benzyloxycarbonyl 1,4-dioxa-8-azaspiro[4,5]decane

To a well-stirred and ice-cooled solution of 1,4-dioxa-8-azaspiro[4,5]decane (34.9 mmol, 5 g) in dichloromethane (200 mL) under an argon atmosphere, was added triethylamine (52.4 mmol, 7.3 mL) and then benzyloxycarbonyl chloride (42 mmol, 5.93 mL) dropwise. The suspension was stirred at room temperature for 24 hours and the precipitated solid was filtered. The organic solution was evaporated under vacuum to give an oily residue which was chromatographed on silica gel eluting with ethyl ether and petroleum ether mixture to afford 8-benzyloxycarbonyl 1,4-dioxa-8-azaspiro [4,5]decane in quantitative yield.

1H-NMR (CDCl$_3$): 1.63 (m, 4H); 3.56 (m,4H); 3.89 (s, 4H); 5.09 (s, 2H); 7.28 (s, 5H).

B. Preparation of the 1-benzyloxycarbonyl piperidin-4-one

To a stirred solution 8-benzyloxycarbonyl 1,4-dioxa-8-azaspiro[4,5]decane (0.037 mol, 10 g) in tetrahydrofuran (150 mL) was added a solution of hydrochloric acid 5% (20 mL) dropwise a room temperature. The solution was stirred for 18 h (TLC control) and then evaporated under vacuum to small volume (20 mL) and neutralized with saturated sodium bicarbonate solution. The aqueous solution was extracted with ethyl acetate (3×100 mL) and the organic layers were dried on sodium sulfate and finally evaporated under vacuum to give 1-benzyloxycarbonyl piperidin-4-one practically pure which was then used in the next step without any further purification (92% yield).

1H-NMR (CDCl$_3$): 1.63 (m, 4H); 3.56 (m,4H); 5.09 (s, 2H); 7.28 (s, 5H).

C. 2-Amino-3-benzoyl-6-benzyloxycarbonyl-4,5,6,7-tetrahydrothieno[2,3-c]pyridine A mixture of equimolar amounts of 1-benzyloxycarbonyl piperidine (0.01 mol), benzoyl acetonitrile (0.01 mol), sulfur (0.01 mol) and morpholine (0.01 mol) in ethanol (4 mL) was stirred and heated at 60° C. for 1 h (TLC control). After this time, the suspension was standing overnight and the mixture is poured into water and the precipitated solid is extracted with ethyl acetate (3×50 mL). The organic layers were dried on magnesium sulfate and evaporated under vacuum. The crude product was chromatographed on silica gel column using mixtures of ethyl acetate and petroleum ether.

(m.p. 138–140° C., 80% yield). 1H-NMR(CDCl$_3$):1.92 (m, 2H), 3.42 (t, 2H); 4.43 (s, 2H); 5.14 (s, 2H); 6.87 (sb, 2H); 7.35–7.46 (m, 5H).

Example 8

2-Amino-3-benzoyl-4,5,6,7-tetrahydrothieno[2,3-c]pyridine

Compound 8

To a cooled and stirred suspension of protected 2-amino-3-benzoyl-6-benzyloxycarbonyl4,5,6,7-tetrahydrothieno[2,3-c]pyridine (0.01 mol) in acetic acid (2 mL), as prepared in Example 7, was added a solution of HBr (33%) in acetic acid (10 mL). After stirring at room temperature for 4 h (TLC control), n-hexane was added and the resulting suspension was evaporated under vacuum to give a solid which was dissolved in water (10 mL) and neutralized with NaOH (5% solution). The precipitated solid was chromatographed on a silica gel column eluting with an ethyl acetate and petroleum ether mixture to give 2-amino-3-benzoyl-4,5,6,7-tetrahydrothieno[2,3-c]pyridine.

(m.p.160–162° C., 92% yield). 1H-NMR (CDCl$_3$): 1.86 (m, 1 H); 1.95 (m, 2H); 2.79 (t, 2H); 3.79 (s, 2H).

Example 9

2-Amino-3-(4-chloro-benzoyl)-6-benzyloxycaronyl-4,5,6,7-tetrahydrothieno[2,3-c]pyridine Compound 9

The procedure of Example 7 was followed except that a corresponding amount of the 4-chloro-derivative of benzoyl acetonitrile was used in place of benzoyl acetonitrile to yield 2-amino-3-(4-chloro-benzoyl)-6-benzyloxycarbonyl-4,5,6,7-tetrahydrothieno[2,3-c]pyridine.

(m.p. 60–62° C., 88% yield). 1H-NMR (CDCl$_3$):1.94 (m, 2H), 3.45 (t, 2H); 4.44 (s, 2H); 5.16 (s, 2H); 6.85 (sb, 2H); 7.36–7.45 (m, 4H).

Example 10

2-Amino-3-(4-chloro-benzoyl) 4,5,6,7-tetrahydrothieno[2,3-c]pyridine

Compound 10

The procedure of Example 8 was followed except that a corresponding amount of 2-amino-3-(4-chloro-benzoyl)-6-benzyloxycarbonyl-4,5,6,7-tetrahydrothieno[2,3-c]pyridine, prepared as in Example 9, was used in place of 2-amino-3-benzoyl-6-benzyloxycarbonyl-4,5,6,7-tetrahydrothieno[2,3-c]pyridine.

(m.p. 164–166° C., 90% yield). 1 H-NMR (CDCl$_3$): 1.74 (m, 1 H); 1.89 (m, 2H); 2.84 (t, 2H); 3.82 (s, 2H); 6.85(sb, 2H), 7.29–7.48 (m, 5H).

Example 11

2-Amino-3-[3-(trifluoromethyl)-benzoyl]-6-(3-phenylprop-1-yl)-4,5,6,7-tetrahydrothieno[2,3-c]pyridine Compound 11

A mixture of equimolar amounts of 3-phenylpropylpiperidin-4-one (0.01 mol) (prepared by a procedure corresponding to that of Example 7, Steps A and B), 3-trifluoromethyl benzoyl acetonitrile (0.01 mol), sulfur (0.01 mol) and morpholine (0.01 mol) in ethanol (4 mL) was stirred and heated at 60° C. for 1 hour (TLC control). After this time, the suspension was allowed to stand overnight and the mixture was poured into water and the precipitated solid was extracted with ethyl acetate (3×50 mL). The organic layers were dried on magnesium sulfate and evaporated under vacuum. The crude product was chromatographed on silica gel column using mixtures of ethyl acetate and petroleum ether.

(m.p.176–178° C.; 78% yield). 1H-NMR (CDCl$_3$): 1.88–2.00 (m, 4H); 2.45–2.71 (m, 6H); 3.44 (s, 2H);6.83(sb, 2H); 7.17–7.48 (m, 9H).

Example 12

2-Amino-3-(4-chloro-benzoyl)-6-(phenylmethyl)-4,5,6,7-tetrahydrothieno[2,3-c]pyridine Compound 12

The same procedure as Example 11 was used except that a corresponding amount of benzylpiperidin-4-one was used in place of 3-phenylpropylpiperidin-4-one and a corresponding amount of 4-chlorobenzoyl acetonitrile was used in place of 3-trifluoromethyl benzoyl acetonitrile.

(m.p.155–157° C.; 78% yield).

Example 13

2-Amino-3-[3-(fluoromethyl)-benzoyl]-6-(phenylmethyl)-4,5,6,7-tetrahydrothieno[2,3-c]pyridine Compound 13

The same procedure as Example 11 was used except that a corresponding amount of benzylpiperidin-4-one is used in place of 3-phenylpropylpiperidin-4-one.

(m.p. 58–60° C.; 88% yield). 1 H-NMR (CHCl$_3$): 1.78–1.87 (m, 2H); 2.48 (t, 2H); 3.42 (s, 2H); 3.63 (s,2H) ;7.01 (sb, 2H); 7.28–7.74 (m, 9H).

Example 14

2-Amino-3-(4-chloro-benzoyl)-6-(2-phenyleth-1-yl)-4,5,6,7-tetrahydrothieno[2,3-c]pyridine Compound 14

The same procedure as Example 11 was used except that a corresponding amount of phenylethylpiperidin-4-one was used in place of 3-phenylpropylpiperidin-4-one and a corresponding amount of 4-chlorobenzoyl acetonitrile was used in place of 3-trifluoromethyl benzoyl acetonitrile.

(m.p. 148–150° C.; 62% yield).

Example 15

2-amino-3-[3-(trifluoromethyl)-benzoyl]-6-(2-phenyleth-1-yl)-4,5,6,7-tetrahydrothieno[2,3-c]pyridine Compound 15

The same procedure as Example 11 was used except that a corresponding amount of benzylpiperidin-4-one was used in place of 3-phenylpropylpiperidin-4-one.

(m.p. 137–138° C.; 81 % yield). 1H-NMR (CHCl$_3$): 1.89 (m, 2H); 2.54 (t, 2H); 2.67–2.87 (m, 4H); 3.51 (s, 2H); 6.99 (sb, 2H); 7.17–7.33 (m, 5H); 7.53–7.74 (m, 4H).

Example 16

2-Amino-3-(4-chloro-benzoyl)-6-(3-phenylprop-1-yl)-4,5,6,7-tetrahydrothieno[2,3-c]pyridine Compound 16

The same procedure as Example 11 was used except that a corresponding amount of 4-chlorobenzoyl acetonitrile was used in place of 3-trifluoromethyl benzoyl acetonitrile.

(m.p. 98–100° C.; 65% yield).

Example 17

2-Amino-3-benzoyl-6-methyl-4,5,6,7-tetrahydrothieno[2,3-c]pyridine

Compound 17

2-Amino-3-benzoyl-4,5,6,7-tetrahydrothieno[2,3-c]pyridine (2 mmol), as prepared in Example 8, and methyl iodide (3 mmol) were dissolved in dry dimethyformamide (20 mL). Finely ground anhydrous potassium carbonate (1.9 g) and sodium iodide (0.2 g) were added to the solution and the resulting mixture was warmed to 65° C. overnight under nitrogen. After this period (TLC control), the reaction mixture was cooled, diluted with water, extracted with diethyl ether (3–50 mL), and dried on sodium sulfate. The crude product was isolated and then purified by column chromatography eluting with ethyl acetate and petroleum ether solutions to give the desired compound.

(m.p. 164–165° C.; 77% yield).

Example 18

2-Amino-3-(4-chloro-benzoyl)-6-(ethoxycarbonylmethyl)-4,5,6,7-tetrahydrothieno[2,3-c]pyridine Compound 18

The same procedure as in Example 17 was used except an equivalent amount of 2-amino-3-(4-chloro-benzoyl)-4,5,6,7-tetrahydrothieno[2,3-c]pyridine was used in place of 2-amino-3-benzoyl-4,5,6,7-tetrahydrothieno[2,3-c]pyridine (2 mmol), and an equivalent amount of ethoxycarbonylmethyl iodide was used in place of methyl iodide (3 mmol).

(m.p. 105–106° C.; 70% yield).

Example 19

2-Amino-3-benzoyl-6-(ethoxycarbonylmethyl)-4,5,6,7-tetrahydrothieno[2,3-c]pyridine Compound 19

The same procedure as in Example 17 was used except an equivalent amount of ethoxycarbonylmethyl iodide was used in place of methyl iodide (3 mmol).

(m.p. 115–117° C.; 83% yield).

Example 20

2-Amino-3-benzoyl-6-(3-methylbut-2-en-lyl)-4,5,6,7-tetrahydrothieno[2,3-c]pyridine Compound 20

The same procedure as in Example 17 was used except an equivalent amount of dimethylallyl iodine was used in place of methyl iodide (3 mmol).

(m.p. 76–78° C. 90% yield). 1H-NMR (CDCl$_3$): 1.63 (s, 3H); 1.73 (s, 3H); 1.94 (m, 2H)); 2.44 (t, 2H); 3.06 (d, 2H); 3.42 (s, 2H); 5.26 (t, 1 H); 6.80 (sb, 2H); 7.35–7.50 (m, 5H).

Example 21

2-Amino-3-(4-chloro-benzoyl)-6-[4-nitro-(2-phenyleth-1-yl)]-4,5,6,7-tetrahydrothieno[2,3-c]pyridine Compound 21

The same procedure as in Example 17 was used except an equivalent amount of 2-amino-3-(4-chloro-benzoyl) 4,5,6,7-tetrahydrothieno[2,3-c]pyridine was used in place of 2-Amino-3-benzoyl-4,5,6,7-tetrahydrothieno[2,3-c]pyridine (2 mmol), and an equivalent amount of p-nitrophenylethyl iodide was used in place of methyl iodide (3 mmol).

(m.p. 150–152° C.; 72% yield).

Example 22

2-Amino-3-benzoyl-6-[4-nitro-(2-phenyleth-1-yl)]-4,5,6,7-tetrahydrothieno[2,3-c]pyridine Compound 22

The same procedure as in Example 17 was used except an equivalent amount of p-nitrophenylethyl iodide was used in place of methyl iodide (3 mmol).

(m.p. 89–91° C.; 70% yield).

Example 23

2-Amino-3-benzoyl-6-[2-t-butoxycarbonylamino-3-(4-hydroxyphenyl)-propion-1-yl]4,5,6,7-tetrahydrothieno[2,3-c]pyridine Compound 23

To an ice-cooled and stirred solution of 2-amino-3-benzoyl-4,5,6,7-tetrahydrothieno[2,3-c]pyridine (0.775 mmol) in dry DMF (11 mL), was added BOC-Tyr-OH (0.08 mmol) and EDCl (0.08, 0.445 g) under an argon atmosphere. After stirring overnight, the mixture was evaporated under vacuum to give a solid residue, which was dissolved in a saturated sodium bicarbonate solution and is extracted with ethyl acetate (3×20 mL), then dried on magnesium sulfate. The organic layers were evaporated under vacuum to give a solid which is chromatographed on silica gel column eluting with ethyl acetate and petroleum ether to afford 2-amino-3-benzoyl-6-[2-t-butoxycarbonylamino-3-(4-hydroxyphenyl)-propion-1-yl]-4,5,6,7-tetrahydrothieno[2,3-c]pyridine as a yellow solid.

(m.p. 143–145° C., 84% yield).

Example 24

2-Amino-3-benzoyl-4,5,6,7-tetrahydrobenzo[b]thiophene

Compound 24

The same procedure as in Example 1 was used except a corresponding amount of cyclohexanone was used in place of methylethyl ketone.

(m.p.150–152° C., 75% yield). 1H-NMR (CDCl$_3$) :1.46–1.49 (m,2H), 1.69–1.80 (m,4H); 2.47–2.54 (m, 2H); 6.71 (sb, 2H); 7.37–7.50 (m, 5H).

Example 25

4-Phenyl-5,6,7,8-tetrahydro[1]benzothieno[2,3-d]pyrimidine

Compound 25

A suspension of 2-amino-3-thienyl)-phenylmethanone (5 mmol) in formamide (7mL) was heated at 180° C. for 5 hours in an open vessel. The residue was diluted with dimethylformamide (5 mL), treated with charcoal, and filtered over a small pad of Celite 503 (brand of filter aid). The cyclized compound was precipitated by addition of water (30 mL) to the filtrate and recrystallized from the same solvents.

(m.p. 135–137° C.).

Example 26

2-Methyl,3-ethoxycarbonyl-4-phenyl-5,6,7,8-tetrahydro[1]benzothieno[2,3-b]pyridine Compound 26

To an ice-cooled and stirred solution of 2-amino-3-thienyl)-phenylmethanone in absolute ethanol (20 mL), ethyl acetoacetate (0.055 mol) was added. To the mixture sodium ethylate (100 mg) was added at 0° C. and the solution was refluxed for about 10 hours. After completion of the reaction (TLC control), the solution was evaporated under vacuum and the residue was taken up with water (50 mL) and the aqueous solution was extracted with ethyl acetate (3×100 mL). The combined organic layers were dried and evaporated under vacuum to give a yellow residue which was crystallized from tetrahydrofuran/hexane.

(m.p. 118–120° C.).

Example 27

2-Amino-3-(4-bromobenzoyl)-cyclopenta[b]thiophene

Compound 27

The same procedure as in Example 1 was used except a corresponding amount of cyclopentanone was used in place of methylethyl ketone and an equivalent amount of 4-bromo-benzoyl acetonitrile was used in place of benzoyl acetonitrile. (m.p. 205–206° C., 87% yield). (CDCl$_3$) :2.1–2.13 (m, 4H), 2.63–2.68 (m, 2H); 6.99 (sb, 2H); 7.34 (d,2H);7.53 (d, 2H).

Example 28

2-Amino-3-benzoyl-6-(4-methylphenylsulphonyl)-4,5,6,7-tetrahydrothieno[2,3-c]pyridine Compound 28

To a well-stirred and ice-cooled solution of 2-amino-3-benzoyl-4,5,6,7 -tetrahydrothieno[2,3-c]pyridine (0.78 mmol, 0.2 g) in dichloromethane (20 ml) under an argon atmosphere, was added triethylamine (0.162 ml) and then p-toluenesulphonyl chloride (0.93 mmol, 177 mg) portionwise. The suspension was stirred a room temperature for 24 h and the precipitated solid was filtered. The organic solution was evaporated under vacuum to give a solid residue which was chromatographed on silica gel eluting with an ethyl ether and petroleum ether mixture to afford 2-amino-3-benzoyl-6-(4-methylphenylsulphonyl)-4,5,6,7-tetrahydrothieno[2,3-c]pyridine.

(m.p.165–167° C., 85 yield). 1 H-NMR (CDCl$_3$): 1.95 (m, 2H); 2.43 (s, 3H); 3.07 (t, 2H); 3.51 (s, 2H); 6.76 (sb, 2H); 7.3–7.67 (m, 9H).

Example 29

4-Phenyl-thieno[2,3-d]pyrimidine

Compound 29

The same procedure as in Example 25 was used except a corresponding amount of 2-amino-3-benzoyl-cyclopenta[b]thiophene was used in place of 2-amino-3-thienyl-phenylmethanone (5 mmol). In turn, 2-amino-3-benzoyl-cyclopenta[b]thiophene can be prepared by the procedure of Example 1.

Example 30

Pharmaceutical Formulations (A) Transdermal System—for 1000 patches

| Ingredients | Amount |
|---|---|
| Active compound | 100 g |
| Silicone fluid | 450 g |
| Colloidal silicon dioxide | 2 g |

The silicone fluid and active compound are mixed together and the colloidal silicon dioxide is added to increase viscosity. The material is then dosed into a subsequent heat sealed polymeric laminate comprised of the following: polyester release liner, skin contact adhesive composed of silicone or acrylic polymers, a control membrane which is a polyolefin, and an impermeable backing membrane made of a polyester multilaminate. The resulting laminated sheet is then cut into 10 sq. cm patches (B) Oral Tablet—For 1000 Tablets

| Ingredients | Amount |
| --- | --- |
| Active compound | 50 g |
| Starch | 50 g |
| Magnesium Stearate | 5 g |

The active compound and the starch are granulated with water and dried. Magnesium stearate is added to the dried granules and the mixture is thoroughly blended. The blended mixture is compressed into tablets.

(C) Injection—for 1000, 1 mL Ampules

| Ingredients | Amount |
| --- | --- |
| Active compound | 10 g |
| Buffering Agents | q.s. |
| Propylene glycol | 400 mg |
| Water for injection | q.s. 1000 mL |

The active compound and buffering agents are dissolved in the propylene glycol at about 50° C. The water for injection is then added with stirring and the resulting solution is filtered, filled into ampules, sealed and sterilized by autoclaving.

(D) Continuous Injection—for 1000 mL

| Ingredients | Amount |
| --- | --- |
| Active compound | 10 g |
| Buffering agents | q.s. |
| Water for injection | q.s. 1000 mL |

What is claimed is:

1. A method of moderating adenosine receptors in a mammal, including a human, comprising the administration to the mammal of an amount of a compound sufficient to modulate adenosine receptors, wherein the compound has the following formula:

wherein:
$R_2$, $R_3$, and $R_4$ are independently hydrogen, halogen, lower alkyl, phenyl, lower alkenyl, lower alkanoyl, amino, trifluoromethyl, amino lower alkyl, nitro, or cyano;
$R_5$ and $R_6$ are independently hydrogen, lower alkyl, or taken together form a lower alkenyl ring of 5 or 6 members,
provided that if $R_2$, $R_3$, and $R_4$ are hydrogen, then, both $R_5$ and $R_6$ may be neither hydrogen nor methyl; further provided that if $R_2$ and $R_3$ are hydrogen while $R_4$ is trifluoromethyl or if $R_2$ and $R_4$ are hydrogen while $R_3$ is chloro, then both $R_5$ and $R_6$ may not be methyl;
$R_7$ is hydrogen or lower alkyl;
Y is nitrogen, CH or C—$COOR_8$; and
$R_8$ is hydrogen or lower alkyl.

2. The method of claim 1 wherein the modulation of the adenosine receptors protects against hypoxia and ischemia induced injury.

3. A method of treating adenosine-sensitive cardiac arrhythmias in a mammal comprising the administration to the mammal of an amount of a compound sufficient to modulate adenosine receptors, wherein the compound has the following formula:

wherein:
$R_2$, $R_3$, and $R_4$ are independently hydrogen, halogen, lower alkyl, phenyl, lower alkenyl, lower alkanoyl, amino, trifluoromethyl, amino lower alkyl, nitro, or cyano;
$R_5$ and $R_6$ are independently hydrogen, lower alkyl, or taken together form a lower alkenyl ring of 5 or 6 members,
provided that if $R_2$, $R_3$ and $R_4$ are hydrogen, then, both $R_5$ and $R_6$ may be neither hydrogen nor methyl; further rovidod that if $R_2$ and $R_3$ are hydrogen while $R_4$ is trifluoromethyl or if $R_2$ and $R_4$ are hydrogen while $R_3$ is chloro, then both $R_5$ and $R_6$ may not be methyl;
$R_7$ is hydrogen or lower alkyl;
Y is nitrogen, CH or —C—$COOR_8$; and
$R_8$ is hydrogen or lower alkyl.

4. A method of treating convulsions in a mammal comprising the administration to the mammal of an amount of a compound sufficient to modulate adenosine receptors, wherein the compound has the following formula:

wherein:
$R_2$, $R_3$, and $R_4$ are independently hydrogen, halogen, lower alkyl, phenyl, lower alkenyl, lower alkanoyl amino, trifluoromethyl, amino lower alkyl, nitro, or cyano;
$R_5$ and $R_6$ are independently hydrogen, lower alkyl, or taken together form a lower alkenyl ring of 5 or 6 members, provided that if $R_2$ and $R_3$ are hydrogen, then, both $R_5$ and $R_6$ may be neither hydrogen nor methyl; further provided that if $R_2$ and $R_3$ are hydrogen while $R_4$ is trifluoromethyl or if $R_2$ and $R_4$ are hydrogen while $R_3$ is chloro, then both $R_5$ and $R_6$ may not be methyl;

$R_7$ is hydrogen or lower alkyl;

Y is nitrogen, CH or —C—$COOR_8$; and $R_8$ is hydrogen or lower alkyl.

5. The method of claim 1 wherein the modulation of the adenosine receptors is used to reduce nociception.

* * * * *

UNITED STATES PATENT AND TRADEMARK OFFICE
CERTIFICATE OF CORRECTION

PATENT NO. : 5,939,432

DATED : August 17, 1999

INVENTOR(S) : Baraldi, Pier Giovanni

It is certified that error appears in the above-identified patent and that said Letters Patent is hereby corrected as shown below:

On the title page: Item [56]

Other Publications, page 1, second cite, line 2, delete "n Chinese " and insert "in Chinese ";

Other Publications, page 1, fifth cite, line 2, delete extra space after Adenosine and delete "A₁Receptor" and insert --A$_1$ Receptor--;

Other Publications, page 1, fifth cite, line 3, add space after -3;

Other Publications, page 1, sixth cite, line 2, delete "Refperfusion" and add --Reperfusion--;

Other Publications, page 1, sixth cite, line 2, delete "Injusry" and add --Injury--;

Other Publications, page 2, first column, fifth cite, line 2, delete "Adensoine" and add --Adenosine--;

Other Publications, page 2, second column, last cite, final line, delete "Scienc" and add --Science--;

Col 1, line 13, after Because, insert --of--;

Col 1, line 54, after compounds insert --are--;

Col 1, line 54, delete "neurotransmifters" and insert --neurotransmitters--;

Col 2, line 51, delete "or3" and add --or 3--;

Col 3, line 8, delete "CH or C(O)OR$_8$" and insert therefor ---CH or -C-C(O)OR$_8$--;

Col 3, line 14, delete "moderate" and insert --modulate--.

Col 3, line 48, delete "etc" and insert --etc.--.

Col 3, line 63, delete "use" and insert therefor --used--.

UNITED STATES PATENT AND TRADEMARK OFFICE
CERTIFICATE OF CORRECTION

PATENT NO. : 5,939,432

DATED : August 17, 1999

INVENTOR(S) : Baraldi, Pier Giovanni

It is certified that error appears in the above-identified patent and that said Letters Patent is hereby corrected as shown below:

Col 4, line 17, delete "or3" and insert --or 3--.

Col 5, line 8, delete "know" and insert --known--;

Col 5, line 49, after Step 1, insert --,--;

Col 5, line 50, delete "present", and

Col 5, line 52, delete "C." and insert --C--;

Col 5, line 59, after groups insert --,--'

Col 5, line 63, delete "Compound" and insert --Compounds--;

Col 8, line 23, after C delete "." and insert --,--;

Col 8, line 28, after C delete ".";

Col 8, line 37, delete "derivative" and insert --derivatives--;

Col 8, line 38, delete "are" and insert --is--;

Col 8, line 39, after desired, insert --,--;

Col 8, line 48, delete "antinociception" and insert --Antinocieption--;

Col 8, line 49, delete "anticonvulsants" and insert --Anticonvulsants--;

Col 9, line 14, delete "$A_1$,AdoR" and insert --$A_1$ AdoR--;

Col 12, line 9, after C, delete ".";

Col 12, line 13, delete "are" and insert --were--;

UNITED STATES PATENT AND TRADEMARK OFFICE
CERTIFICATE OF CORRECTION

PATENT NO. : 5,939,432
DATED : August 17, 1999
INVENTOR(S) : Baraldi, Pier Giovanni Page 3 of 6

It is certified that error appears in the above-identified patent and that said Letters Patent is hereby corrected as shown below:

Col 12, line 17, delete "C.," and insert --C;--;

Col 12, line 34, after C, delete ".";

Col 12, line 39, after C, delete ".";

Col 12, line 43, after C, delete ".";

Col 12, line 46, after C, delete ".";

Col 12, line 50, after C, delete ".";

Col 13, line 3, delete " 8-benzyloxycarbonyl 1," and insert --8-benzyloxycarbonyl-1--;

Col 13, line 9, delete " 8-benzyloxycarbonyl 1," and insert --8-benzyloxycarbonyl-1--;

Col 13, line 29, after C, delete ".";

Col 13, line 31, after solid, delete "is" and insert --was--;

Col 13, line 34, after on, insert --a--;

Col 13, line 36, after 140°, delete " C.," and insert --C,--;

Col 13, line 57, after 162°, delete "C.," and insert --C--;

Col 14, line 19, delete " C.," and insert --C,--;

Col 14, line 35, after C delete ".";

Col 14, line 43, after C delete ".";

Col 14, line 57, after C delete ".";

Col 14, line 66, delete " is " and insert --was--;

UNITED STATES PATENT AND TRADEMARK OFFICE
CERTIFICATE OF CORRECTION

PATENT NO. : 5,939,432
DATED : August 17, 1999
INVENTOR(S) : Baraldi, Pier Giovanni It is certified that error appears in the above-identified patent and that said Letters Patent is hereby corrected as shown below:

Col 15, line 1, after C delete ".";

Col 15, line 1, remove extra space before H-NMR;

Col 15, line 2, delete "(s,2H)" and insert --(s, 2H); line 3, delete ";".

Col 15, line 15, after C delete ".";

Col 15, line 27, after C delete ".";

Col 15, line 39, after C delete ".";

Col 15, line 51, after C delete ".";

Col 15, line 58, after C delete ".";

Col 16, line 5, after C delete ".";

Col 16, line 17, after C delete ".";

Col 16, line 28, delete "C." and add --C;--;

Col 16, line 46, after C delete ".";

Col 16, line 57, after C delete ".";

Col 17, line 2, delete "0.08," and insert --(0.08mmo),--; 3, delete "mmol"

Col 17, line 5, delete "is" and insert --was--;

Col 17, line 8, delete "is" and insert --was--;

Col 17, line 8, delete "on silica" and insert --on a silica--;

Col 17, line 13, after C delete ".";

Col 17, line 23, after C delete ".";

UNITED STATES PATENT AND TRADEMARK OFFICE
CERTIFICATE OF CORRECTION

PATENT NO. : 5,939,432

DATED : August 17, 1999

INVENTOR(S) : Baraldi, Pier Giovanni

It is certified that error appears in the above-identified patent and that said Letters Patent is hereby corrected as shown below:

Col 17, line 23, delete extra space before 75%;

Col 15, line 1, after C delete ".";

Col 17, line 24, delete "(m,2H)" and insert --(m, 2H)--;

Col 17, line 24, delete "(m,4H)" and insert --(m, 4H)--;

Col 17, line 34, after C delete ".";

Col 17, line 41, after C delete ".";

Col 17, line 51, delete space before C and after C delete ".";

Col 17, line 59, after C delete ".";

Col 18, line 3, delete space before C and after C delete ".";

Col 18, line 5, delete "(d,2H)" and add --(d, 2H)--;

Col 18, line 16, delete "7 -tetrahydrothieno[" and
   insert --7-tetrahydrothieno[--:

Col 18, line 28, after C delete ".";

Col 19, line 36, delete "moderating" and
   insert --modulating--;

Col 19, line 62, delete "then," and insert --then--;

Col 20, line 35, delete "rovidod" and insert --provided--;

Col 20, line 40, delete "-C-COOR$_3$" and insert --C-COOR$_8$--;

Col 22, line 1, delete "-C-COOR$_3$" and insert --C-COOR$_8$--.

UNITED STATES PATENT AND TRADEMARK OFFICE
CERTIFICATE OF CORRECTION

PATENT NO.    :    5,939,432

DATED         :    August 17, 1999

INVENTOR(S)   :    Baraldi, Pier Giovanni

It is certified that error appears in the above-identified patent and that said Letters Patent is hereby corrected as shown below:

In Other Publications, page 1, sixth cite, line 1, insert therefor --.-- after X;

In Other Publications, page 2, fifth cite, line 1, delete "Cardia" and insert therefor --Cardiac--;

In Other Publications, page 2, sixth cite, line 1, delete "Pcychotropic" and insert therefor -Psychotropic--;

Col. 5, line 53 and 54, delete " IA" and insert therefor --1A;

Col. 8, line 25, delete "$R_8$" and insert therefor --$R_8'$--;

Col. 10, line 2, delete "pressure" and insert therefor --presence--;

Signed and Sealed this

Seventeenth Day of October, 2000

Q. TODD DICKINSON

*Attest:*

*Attesting Officer*         *Director of Patents and Trademarks*